(12) United States Patent
McGann

(10) Patent No.: US 6,228,122 B1
(45) Date of Patent: May 8, 2001

(54) NET SEMICONSTRAINED DEVICE FOR TOTAL HIP REPLACEMENT STABILITY

(76) Inventor: William A. McGann, 55 20$^{th}$ Ave., San Francisco, CA (US) 94121

( * ) Notice: Subject to any disclaimer, the term of this patent is extended or adjusted under 35 U.S.C. 154(b) by 0 days.

(21) Appl. No.: 09/314,555

(22) Filed: May 19, 1999

Related U.S. Application Data

(60) Provisional application No. 60/085,975, filed on May 19, 1998.

(51) Int. Cl.$^7$ ........................................................ A61F 2/34
(52) U.S. Cl. ..................................... 623/23.11; 623/23.14
(58) Field of Search .............................. 606/151; 623/13, 623/22, 23, 18, 19

(56) References Cited

U.S. PATENT DOCUMENTS

| | | |
|---|---|---|
| 4,731,088 | 3/1988 | Collier . |
| 5,718,012 * | 2/1998 | Cavallaro ............................ 8/94.11 |
| 5,755,807 | 5/1998 | Anstaett et al. . |
| 5,916,585 | 6/1999 | Cook et al. . |
| 5,951,605 * | 9/1999 | Dennis et al. ........................ 623/23 |

OTHER PUBLICATIONS

"Cerclage Cable System" Acumed, Inc. p. 5, Jul. 1992.*

* cited by examiner

Primary Examiner—Henry J. Recla
Assistant Examiner—Anthony S. King
(74) Attorney, Agent, or Firm—Fliesler, Dubb, Meyer & Lovejoy

(57) ABSTRACT

An apparatus and method for hip replacement stability includes a connector which is adapted to be connected between at least one of an acetabular cup, or a component of an acetabular cup, or the adjacent bone, and at least one of a replacement femur or a femur. The connector is flexible and allows for uninhibited movement between an acetabular cup and replacement femur up to a limit in order to prevent dislocation. The connector is in one embodiment comprised of a net. The method of the invention for preventing dislocation between an acetabular cup and replacement femur includes the steps of securing the connector to at least one of an acetabular cup, or a component thereof, or bone located adjacent to an acetabular cup, and securing the connector to at least one of a replacement femur or a femur.

14 Claims, 6 Drawing Sheets

Net connected through polyethylene liner.

Net connected through polyethylene liner, metal shell, and bone

Net connected directly to bone

NET SEMICONSTRAINED DEVICE FOR TOTAL HIP REPLACEMENT STABILITY

The application claims the benefit of U.S. Provisional Application No. 60/085,975, filed May 19, 1998.

FIELD OF THE INVENTION

The present invention is directed to hip replacement systems and components thereof.

BACKGROUND OF THE INVENTION

Total hip replacement is considered the most successful orthopaedic surgical procedure ever devised. Its success has now spanned three decades. There are now approximately 120,000 hip replacements performed in the U.S. each year. About one-third of the operations performed are for revision replacement of previously implanted prosthetic hips. The main cause of revision is for aseptic loosening. Another reason for revision is dislocation of the components. Dislocation continues to be a problem in total hip replacement. Every surgeon who performs this operation has this complication, no matter how experienced he or she is with total hip replacement. The incidence of dislocation varies widely in the community. Most experienced surgeons expect less than a 3% incidence. Some community surgeons are known to have as high as 30% dislocation rate. Dislocations are proven to be associated with (i) the type of approach, posterior being the most common—90%, and (ii) whether the case is a revision (three times the incidence over primary replacements). About half of the dislocations occur in the first month after the procedure. The remainder of the dislocations occur over the span of many years. A dislocation can occur at any time in the lifetime of the arthroplasty. It is evident that dislocation remains a problem complication in the most successful orthopaedic procedure ever devised.

Attempts have been made to make the hip replacement operation more stable and thus reduce the incidence of dislocation. To preserve soft tissue attachments posteriorly, the surgical approach has been changed. The "direct lateral approach" has been utilized in the joint replacement, but residual pain, limp, and heterotopic ossification have tempered its use. It is not well proven that the incidence has been dramatically affected despite this change in the approach. Recently, unpublished reports have demonstrated an improved dislocation rate through the reattachment of soft tissues in conjunction with the posterior approach. This technique remains to be proven and additional study is needed. The posterior soft-tissue techniques do not address revision operations, since the soft tissues are deficient or absent in revision cases.

Modification of the components has also been undertaken to try and make the arthroplasty more stable. The use of a locking mechanism between the femoral ball and the acetabular socket has been fraught with problems. This so-called "constrained" socket fails early because of high stresses arising from impingement between the socket and femoral neck. This may cause the socket to pull out from the bone attachment in the pelvis, or dislodge the ring lock holding the devices together. Another modification is the simple addition of a buildup of the polyethylene rim. This modification does not appear to influence the dislocation rate in clinical studies. This is probably because of the reduction of a "safe zone" before impingement occurs between the femoral neck and the rim of the polyethylene socket. On the femoral side, attempts at enlarging the diameter of the femoral head had not influenced the rate of dislocation. Enlarging the femoral head has been unpopular largely because of the problem of increased polyethylene wear seen with large diameter heads.

SUMMARY OF THE INVENTION

The present invention is directed to overcome some of the disadvantages of the prior art. In particular, the present invention is directed toward an apparatus and method for preventing dislocation between an acetabular cup and a replacement femur.

In one aspect of the invention, a device is provided for hip replacement stability. The hip replacement uses an acetabular cup implantable into an adjacent bone and a replacement femur implantable into a femur. The device of the invention includes a connector which is adapted to connect to (1) at least one of an acetabular cup, or a component of an acetabular cup, or the adjacent bone, and (2) at least one of a replacement femur or a femur.

The connector is flexible.

In another aspect of the invention, the connector is adapted for allowing uninhibited movement between an acetabular cup and a replacement femur up to a limit.

In yet a further aspect of the invention, a connector is adapted for preventing a replacement femur from becoming dislocated from an acetabular cup.

In yet a further aspect of the invention, a connector is comprised of a net.

In still a further aspect of the invention, a method is provided for preventing dislocation between an acetabular cup and replacement femur comprising the steps of securing a connector to at least one of an acetabular cup, or a component thereof, or a bone located adjacent to an acetabular cup and securing a connector to at least one of the replacement femur or a femur.

In another aspect of the invention, a method is provided for preventing dislocation which method includes implanting an acetabular cup or component thereof which has selectively secured thereto a connector and selectively securing the connector to one of a replacement femur or a femur.

Other aspects and objects of the invention can be obtained through a review of the specification of the claims and the figures.

DETAILED DESCRIPTION OF A PREFERRED EMBODIMENT OF THE INVENTION

The net of the present invention addresses the problem of dislocation in a new way. It effectively reinforces the total hip replacement by providing tension against the specific forces that lead to dislocation.

Figure 1:
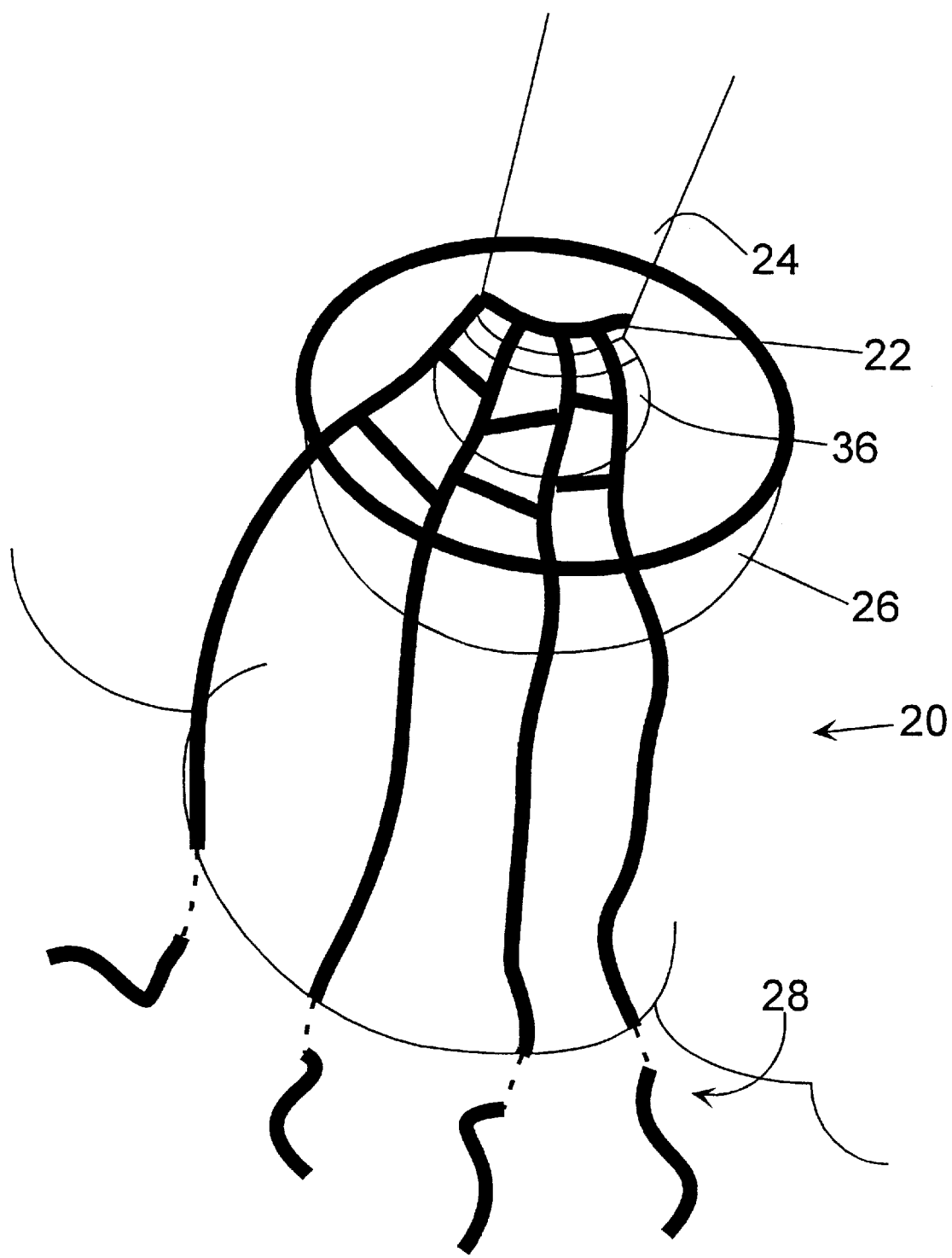
FIG. 1 depicts a schematic drawing of an embodiment of a connector of the invention.

FIG. 1 depicts a schematic diagram of one variation of the net device 20 of the invention. The net device 20 has a ring 22 which secures the net 20 about the replacement femoral neck 24. The net 20 then is attached to the acetabular cup 26 or the bone 28 into which the acetabular cup 26 is implanted. In this embodiment, the net 20 is comprised of a polyethylene material. However, it is to be understood that other materials such as by way of example only, suture materials can be used and be within the spirit and scope of the invention.

This flexible connecting material essentially mimics the normal soft tissue capsule of the hip joint. Importantly, as in the normal hip, the tension is only present at specific positions of the hip joint, and only comes into play when it is needed. During normal activities, the net device 20 is at rest, and is not stressed. This principle is much like the seatbelt in an automobile, that is called into use only when it is required. In the case of a joint replacement which may have a decade or more of use, this factor of only temporary use will allow the device to span many years. The crucial period of usefulness will be in the early postoperative period when the soft tissues are in their healing phase, and are thus at their weakest state. For revision operations, which have limited, or absent soft-tissue response to healing, the net device 20 may be more important for the life of the implant. Adding a biological growth material to the net to stimulate the regrowth of living tissue may restore the biologic stability to the hip replacement, and minimize the utilization of the inert portion of the net device 20 over time.

Figure 2:
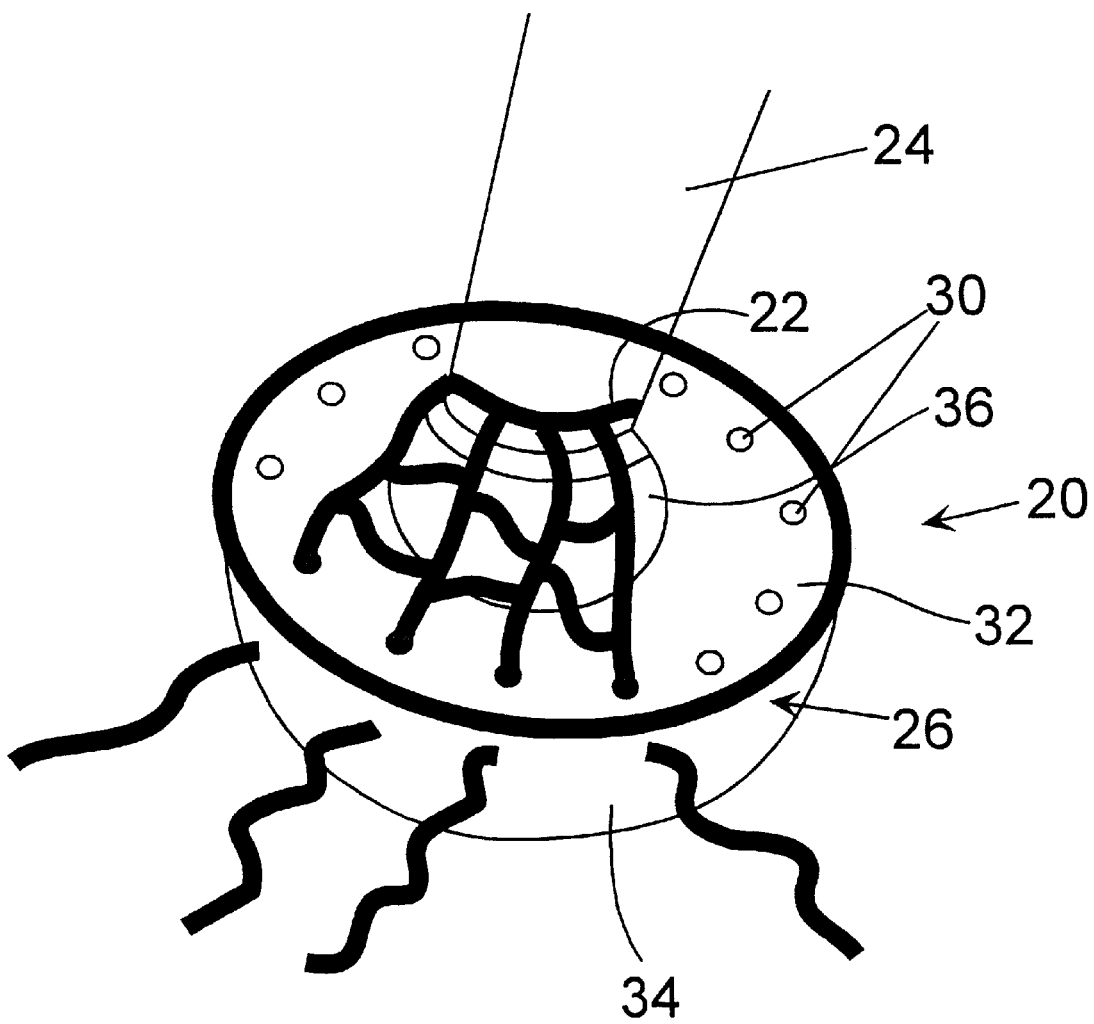
FIG. 2 depicts a figure similar to FIG. 1 with the connector of this embodiment attached through holes of the acetabular cup.

FIG. 2 depicts the net device 20 attached through holes 30 in the acetabular cup 26. The holes 30 are preferably pre-drilled in the insert 32 of the cup 26. As is known in the art, the insert 32 fits into a shell 34 which is secured to the bone of the patient.

Figure 5:
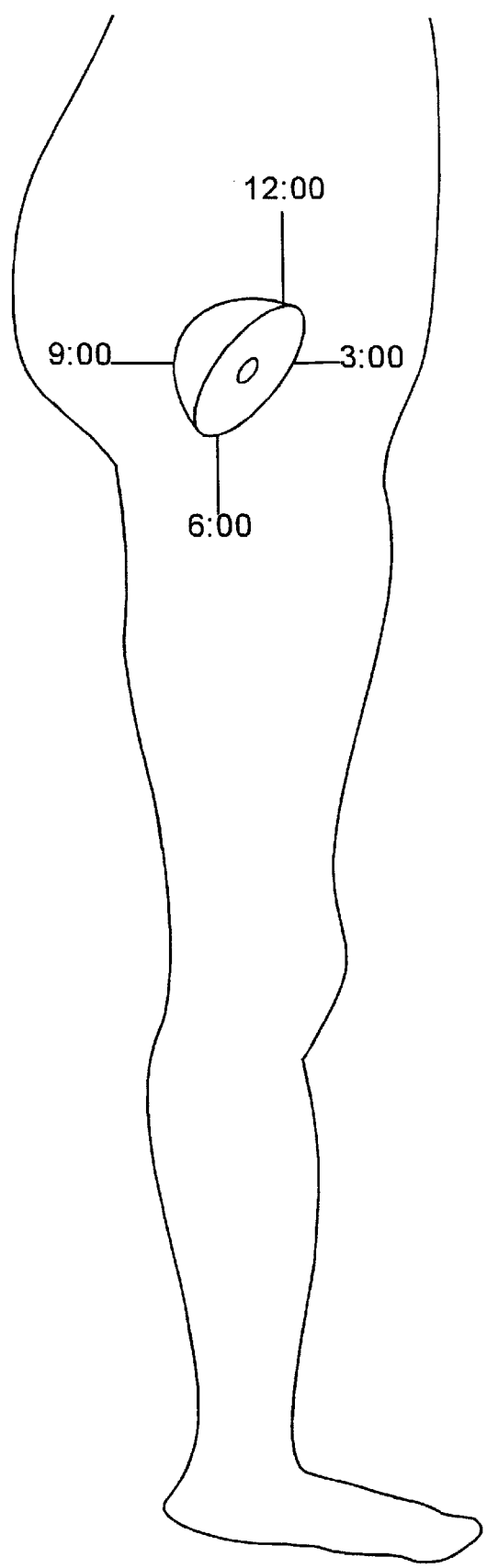
FIG. 5 depicts the various regions where the connector of the invention can be connected to the acetabular cup.

The net can be either pre-set, or tensioned intraoperatively. The advantage of intraoperative tensioning, is to provide specific tension at hip positions that are at risk for dislocation. The position of risk for the more common posterior dislocation is where the hip is (i) flexed, (ii) internally rotated, and (iii) adducted. The number and location of the attachment points of the net 20 to the cup 26 may vary according to the needs of the surgeon. The connections to the socket can be utilized over the posterior, superior, or anterior margin as indicated to correspond to the instability at risk (lack of soft tissue encapsulating the ball and socket joint). Posterior instability generally occur about 90% of the time. As can be seen in FIG. 5, the posterior margin is from about 6:00 to about 12:00 o'clock, the superior margin from about 9:00 to about 3:00 o'clock, and the anterior margin is from about 12:00 at about 6:00 o'clock. Thus, the net 20 can be "called into action" where specifically needed as determined by the surgeon.

In other words, the cup 26 is pre-drilled with holes 30 about the exterior peripheral lip of the cup 26. Only the holes needed to obtain the desired restraint are used to secure the net 20. Further, the length of the strands of the net are adjacent and tied off as appropriate, after the strands are fed through the holes 30. Thus, the net 20 can be positioned where the greatest instability is to provide tension in order to prevent hip dislocation.

The net 20 can be used in both primary and revision total hip procedures. The advantage in revision procedures is noted especially in cases of recurrent dislocation of the hip, where the metal acetabular shell 34 is well fixed to the bone by bone ingrowth. When the metal acetabular shell 34 is well-fixed in the bone, the acetabular liner or insert 32 can be revised with the incorporation of the net 20. Providing the locking mechanism the shell is secure, the new liner 32 with the net 20 can be simply inserted, and the femoral ring 22 attached to the femoral neck, or Morse taper. The net 20 will then provide a mechanism to secure the femoral head 36 in the acetabular cup 26 and allow proper fibrous healing to take place without the risk of dislocation. The net 20 may also eliminate the need for costly external bracing of the limb during the postoperative period. If an insufficient locking mechanism is found between the metal shell 34 and the polyethylene liner 32, then the net 20 can be anchored to the acetabular bone 28 instead of the shell 34 or insert 32.

Figure 6:
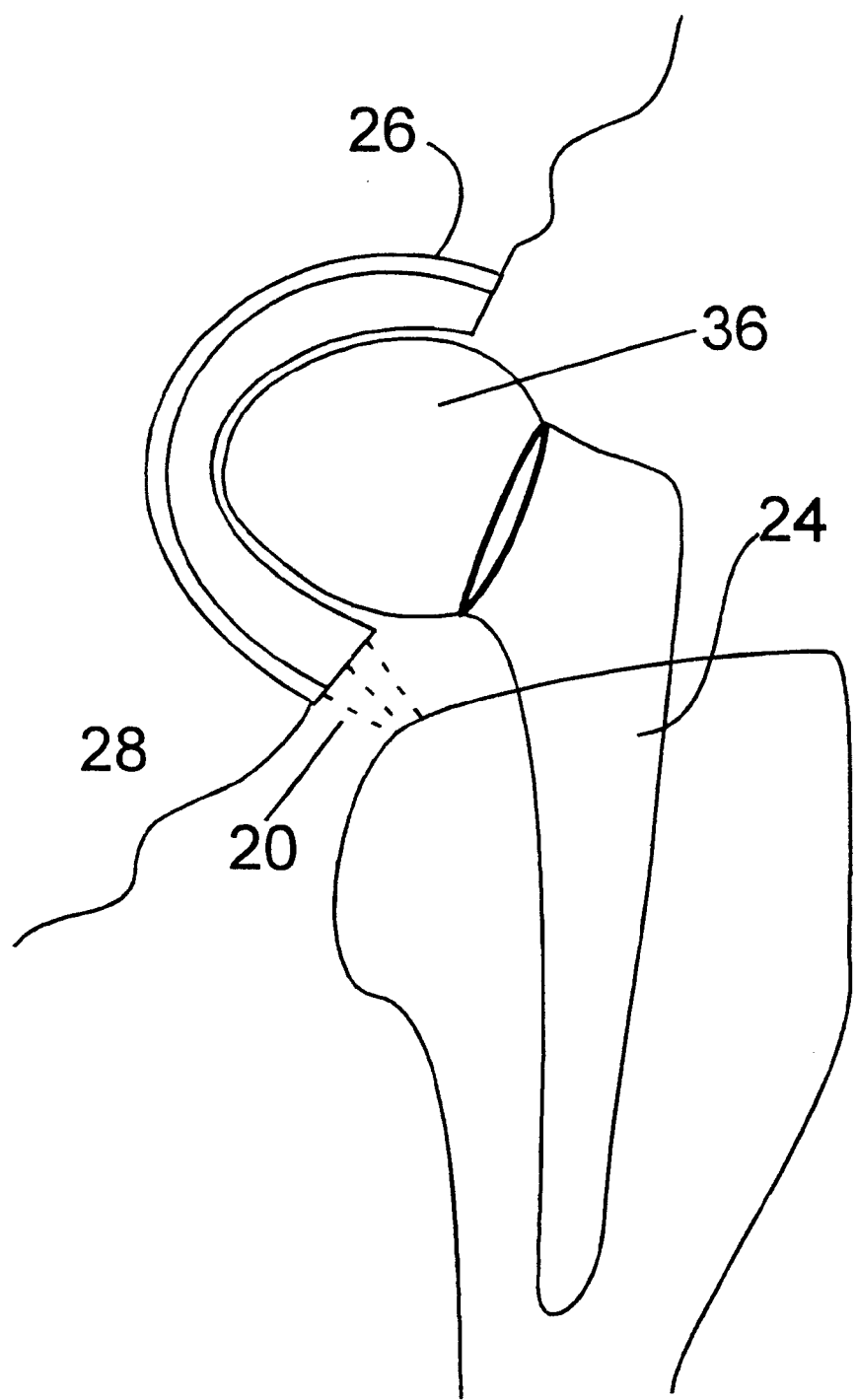
FIG. 6 depicts an embodiment of the invention where the connector is connected to the femur.

Also, the femoral side of the net can also be directly attached to the femoral bone 38 if indicated (FIG. 4a and FIG. 6) instead of using net ring 22.

In primary cases of total hip replacement, where the metal shell 34 is not ingrown, the net 20 can be attached to the acetabular bone 28 instead of the acetabular cup 26. This may be necessary since the metal shell 34 may not be fully secured in the acetabular bone 28 for a few months after its insertion. This early period is the critical time to prevent dislocations from occurring. The metal shell 34 may be press-fitted in place, or may be secured with fixation screws. In some situations, especially with exceptional fixation and quality bone, this may be enough to utilize the net attached to the insert or liner 32 of the cup 26. In cases where bone attachment is necessary, drills may be required to facilitate the tunneling of the net through the posterior wall of the acetabulum.

Figure 3:
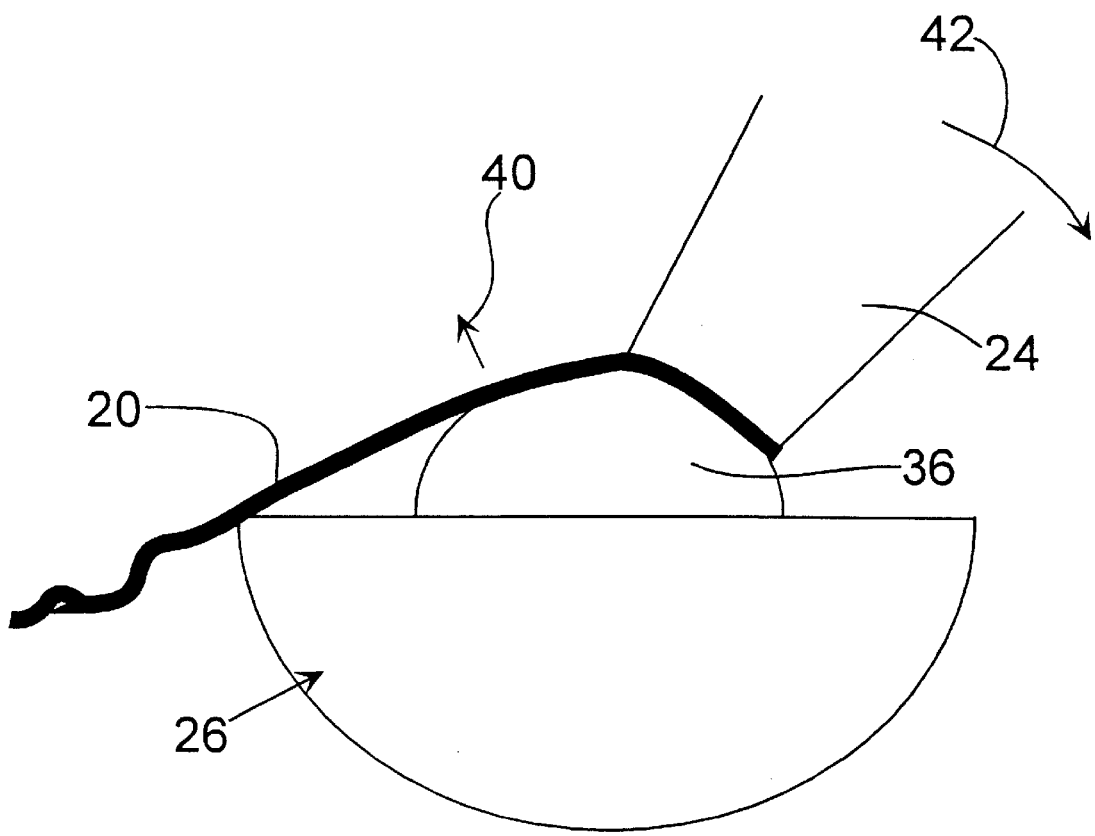
FIG. 3 depicts a side view of the embodiment of FIG. 1.

FIG. 3 depicts how the net 20 tightens up to prevent the hip from dislocating in the direction 40 when the femur is moving in the direction 42.

Figure 4C:
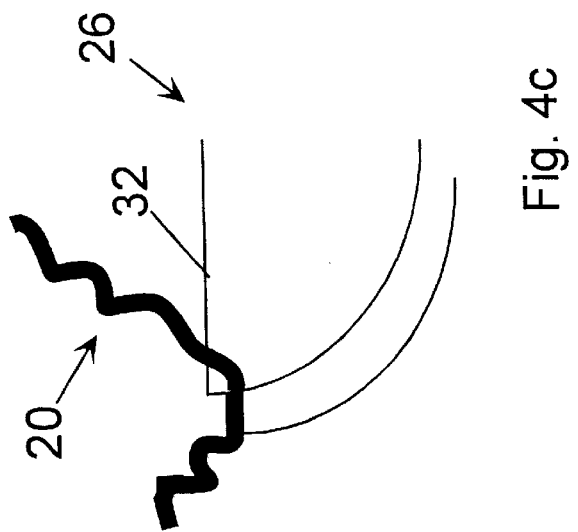
FIGS. 4a, 4b, and 4c demonstrate various methods whereby an embodiment of the invention can be connected to any one of or a combination of the adjacent bone, or the acetabular cup, or components of the acetabular cup including the liner and the metal shelf.
Figure 4B:
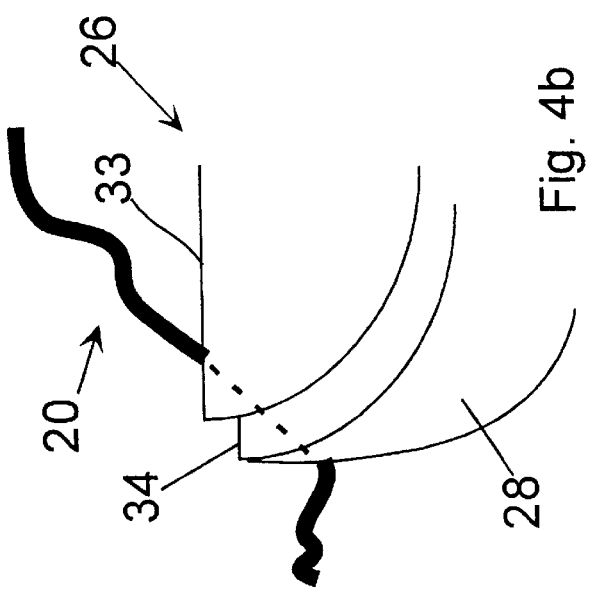
Figure 4A:
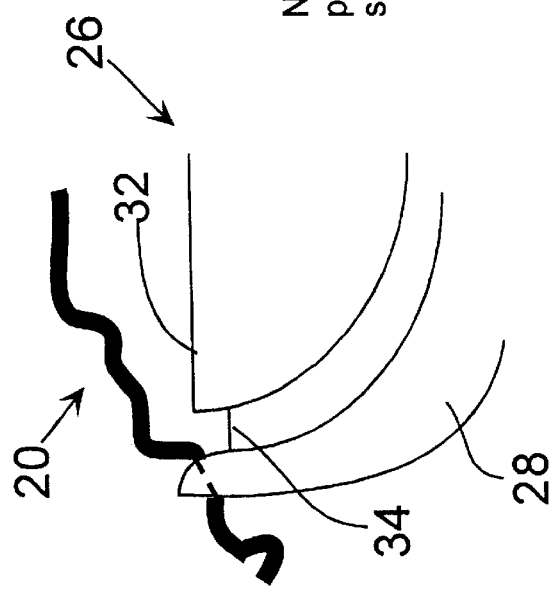

As can be seen in FIGS. 4a, 4b, and 4c, the net 20 can be received (i) through the bone, or (ii) through the polyethylene liner shell and bone or (iii) through the polyethylene liner.

INDUSTRIAL APPLICABILITY

Based on the above, it can be seen that the present invention prevents dislocation of a replacement femur from an acetabular cup. Such prevention greatly increases the success rate and stability of hip implants.

Other features, aspects and objects of the invention can be obtained from a review of the figures and the claims.

It is to be understood that other embodiments of the invention can be developed and fall within the spirit and scope of the invention and claims.

I claim:

1. A device for hip replacement stability which hip replacement uses an acetabular cup implantable into adjacent bone and a replacement femur implantable into a femur, said device comprising:

a connector which is adapted to be connected to (1) at least one of an acetabular cup, or a component of an acetabular cup, or the adjacent bone, and (2) a replacement femur;

wherein said connector is comprised of a plurality of tethers, part of which tethers with cross-members form a net; and wherein said connector has a ring that is adapted to be connected around a neck of a replacement femur; and wherein said plurality of tethers is a attached to and spaced about said ring and are adapted to be connected to said at least one of the acetabular cup, or the component of the acetabular cup, or the adjacent bone.

2. The device of claim 1 wherein:
said connector is flexible.

3. The device of claim 1 wherein:
said connector is adapted for allowing uninhibited movement between an acetabular cup and a replacement femur up to a limit.

4. The device of claim 1 wherein:
said connector is adapted for preventing a replacement femur from becoming dislocated from an acetabular cup.

5. The device of claim 1 wherein:
said connector is comprised of polyethylene.

6. The device of claim 1 wherein:
a biological growth material is added to the connector.

7. The device of claim 1 wherein:
the connector is adapted to be received through holes provided in an acetabular cup or a shell or liner component of an acetabular cup.

8. The device of claim 1 wherein:
the connector is adapted to be connected to at least one of the posterior margin, the superior margin or the anterior margin of an acetabular cup or the adjacent bone.

9. The device of claim 1 wherein:
the length of the connector can be adjusted as is appropriate.

10. A device for hip replacement stability which hip replacement uses an acetabular cup implantable into adjacent bone and a replacement femur implantable into a femur, said device comprising:
a flexible connector which can prevent dislocation between the replacement femur and the acetabular cup and which is adapted to be connected to (1) at least one of an acetabular cup, or a component of an acetabular cup, or the adjacent bone, and (2) a replacement femur; and
wherein said connector includes a plurality of tethers, part of which tethers with cross-members form a net, and which connector has a ring which is adapted to be connected around a neck of a replacement femur; and
wherein said plurality of tethers is attached to and spaced about said ring and are adapted to be connected to said at least one of the acetabular cup, or the component of the acetabular cup, or the adjacent bone.

11. A hip replacement system comprising:
an acetabular cup or component thereof;
a replacement femur;
a connector which is designed to be connected to (1) at least one of an acetabular cup, or a component of an acetabular cup, or the adjacent bone, and (2) a replacement femur; and
said connection includes a plurality of tethers, part of which tethers with cross-members form a net and which connector has a ring that is adapted to be connected around a neck of said replacement femur; and
wherein said plurality of tethers is attached to and spaced about said ring and are adapted to be connected to said at least one of the acetabular cup, or a component of the acetabular cup, or the adjacent bone.

12. A device for ball and socket replacement stability which ball and socket replacement uses a replacement socket implantable into a bone and a replacement ball implantable into another bone, said device comprising:
a connector which is adapted to be connected to (1) at least one of a replacement socket, or a component of a replacement socket or the adjacent bone, and (2) a replacement ball;
wherein said connector is comprised of a plurality of tethers, part of which tethers with cross-members form a net; and
wherein said connector has a ring that is adapted to be connected around a neck of the replacement ball; and
wherein said plurality of tethers is attached to and spaced about said ring and are adapted to be connected to said at least one of the replacement socket, the component of the replacement socket, or the adjacent bone.

13. A device for ball and socket replacement stability which ball and socket replacement uses a replacement socket implantable into a bone and a replacement ball implantable into another bone, said device comprising:
a flexible connector which can prevent dislocation between the replacement ball and the replacement socket and which is adapted to be connected to (1) at least one of the replacement socket or a component of the replacement socket, or the adjacent bone, and (2) a replacement ball; and
wherein said connector includes a plurality of tethers, part of which tethers with cross-members form a net and which connector has a ring which is adapted to be connected around a neck of the replacement ball; ande
wherein said plurality of tethers is attached to and spaced about said ring and are adapted to be connected to said at least one of the replacement socket, the component of the replacement socket or the adjacent bone.

14. A ball and socket replacement system comprising:
a replacement socket;
a replacement ball;
a connector which is designed to be connected to (1) at least one of the replacement socket, or a component of the replacement socket, or the adjacent bone, and (2) the replacement ball, said connection includes a plurality of tethers, part of which tethers with cross-members form a net, and which connector has a ring that is around a neck of the replacement ball; and
wherein said plurality of tethers is attached to and spaced about said ring and are adapted to be connected to said at least one of the replacement socket, the component of the replacement socket, or the adjacent bone.

* * * * *